(12) United States Patent
Ingenbleek et al.

(10) Patent No.: US 8,399,856 B2
(45) Date of Patent: Mar. 19, 2013

(54) METHOD AND DEVICE FOR DETECTING DEGRADATION IN THE QUALITY OF A BRAKE FLUID

(75) Inventors: Gerardus Wilhelmus Henricus Ingenbleek, Amsterdam (NL); Johannes Bernardus Wilhelmus Morsink, Amsterdam (NL)

(73) Assignee: Shell Oil Company, Houston, TX (US)

( * ) Notice: Subject to any disclaimer, the term of this patent is extended or adjusted under 35 U.S.C. 154(b) by 81 days.

(21) Appl. No.: 12/681,928

(22) PCT Filed: Oct. 9, 2008

(86) PCT No.: PCT/EP2008/063564
§ 371 (c)(1),
(2), (4) Date: Apr. 7, 2010

(87) PCT Pub. No.: WO2009/047307
PCT Pub. Date: Apr. 16, 2009

(65) Prior Publication Data
US 2010/0213388 A1   Aug. 26, 2010

(30) Foreign Application Priority Data
Oct. 11, 2007   (EP) .................................... 07118279

(51) Int. Cl.
*G01J 1/58* (2006.01)
(52) U.S. Cl. .................................. 250/459.1; 250/458.1
(58) Field of Classification Search ............... 250/459.1, 250/458.1
See application file for complete search history.

(56) References Cited

U.S. PATENT DOCUMENTS

| | | | |
|---|---|---|---|
| 3,505,020 A * | 4/1970 | Caldwell | 436/40 |
| 4,869,596 A | 9/1989 | Klein et al. | 374/27 |
| 5,380,091 A | 1/1995 | Buchanan | 374/16 |
| 5,785,425 A | 7/1998 | Buchanan | 374/16 |
| 7,122,812 B2 * | 10/2006 | Kalley et al. | 250/504 R |
| 2002/0129644 A1 | 9/2002 | Petty | 73/61.46 |
| 2005/0272844 A1 * | 12/2005 | Westman et al. | 524/366 |
| 2006/0032294 A1 * | 2/2006 | Duerr et al. | 73/40.7 |
| 2007/0087946 A1 * | 4/2007 | Quest et al. | 508/433 |

FOREIGN PATENT DOCUMENTS

| | | |
|---|---|---|
| DE | 3143589 | 5/1983 |
| DE | 19838025 | 2/2000 |
| DE | 10101467 | 7/2002 |
| EP | 0078544 A * | 5/1983 |
| EP | 78544 A1 * | 5/1983 |
| EP | 543057 | 5/1993 |
| FR | 2664701 | 1/1992 |
| WO | WO02068926 | 9/2002 |

OTHER PUBLICATIONS

Choi et al., A Simple Ratiometric Probe System for the Determination of Water Content in Organic Solvents, 2007, Bulletin Korean Chemical Society, vol. 28, pp. 1818-1820.*

* cited by examiner

*Primary Examiner* — Christine Sung

(57) ABSTRACT

A method and a device for detecting degradation in the quality of a brake fluid are disclosed. The brake fluid comprises a luminescent dye, wherein there is a change in luminescence emitted by the dye in response to a change in water content of the brake fluid.

8 Claims, No Drawings

METHOD AND DEVICE FOR DETECTING DEGRADATION IN THE QUALITY OF A BRAKE FLUID

PRIORITY CLAIM

The present application claims priority to European Patent Application 07118279.4 filed 11 Oct. 2007.

FIELD OF THE INVENTION

The invention relates to a method and a device for detecting degradation in the quality of a brake fluid.

BACKGROUND OF THE INVENTION

Brake fluid is used to transmit the pressure exerted on a brake pedal, through hydraulic lines, to the cylinders of a braking mechanism. The most commonly used brake fluids are glycol ether-based liquids that may be blended with polyglycols. These liquids are hygroscopic and will absorb moisture from the atmosphere, which gradually reduces the boiling point of the brake fluid. If the boiling point of the brake fluid is lowered, bubbles of vapour may be produced during braking when friction causes the temperature of the brake fluid to rise. Vapour bubbles impair the functioning of the hydraulic mechanism and this represents a significant safety hazard. Additionally, increased levels of water in brake fluid can negatively impact the low temperature viscosity, the anti-corrosion performance and the elastomer compatibility of the brake fluid.

Several systems are used to determine whether the boiling point of a brake fluid has been compromised by absorption of water. The Equilibrium Reflux Boiling Point (ERBP) method (e.g. as specified by the US Federal Motor Vehicle Safety Standard (FMVSS 116)) is typically used to determine boiling point and Karl Fischer titration (e.g. according to the ASTM standard D1123) may be used to determine water content. These methods are accurate but are labour intensive and must be conducted by a skilled person in a laboratory. Moreover, the ERBP method requires a significant sample quantity making it impractical to apply to a brake fluid while present in a car braking system.

U.S. Pat. No. 5,785,425 and U.S. Pat. No. 5,380,091 both disclose hand held devices for detecting degradation in brake fluid quality that could be used by a car mechanic in a garage. A probe is inserted into the brake fluid and a display indicates the boiling point of the brake fluid to the user.

U.S. Pat. No. 4,869,596 discloses a method for checking the state of a brake fluid contained in a vehicle wherein the boiling point of the braking fluid is measured, the temperature of the braking fluid is measured, and these are compared with standard values. Changes in the brake fluid quality are indicated to the driver of the vehicle, so that the driver is informed of hazardous changes and can take appropriate action.

DE 3143589 discloses a device wherein a colour indicator is brought into contact with a brake fluid, and wherein a colour change indicates the water content of the brake fluid. DE 19838025 discloses brake fluid comprising a colour indicator such that the brake fluid changes colour as the water content of the brake fluid varies. FR 2664701 discloses another method wherein colour indicators are used to indicate the water content of brake fluid.

The present inventors have sought to provide an alternative method and device for detecting degradation in the quality of a brake fluid. Desirably the method and device reliably indicate the presence of water in the brake fluid, without the need for multiple complicated measurements. Most desirably, the method and device allow for detection of water whilst the brake fluid is still present in the braking system (i.e. there is no requirement to remove a sample of the brake fluid from the system so that it can be tested), and preferably the method and device allow for detection of water at or near a wheel cylinder where the presence of water in the brake fluid is most critical.

SUMMARY OF THE INVENTION

Accordingly, the present invention provides a method for detecting degradation in the quality of a brake fluid, wherein the brake fluid comprises a luminescent dye, wherein there is a change in luminescence emitted by the dye in response to a change in water content of the brake fluid, comprising a step of detecting changes in the luminescence emitted by the dye.

In a further aspect, the present invention provides a brake fluid comprising a luminescent dye, wherein there is a change in luminescence emitted by the dye in response to a change in water content of the brake fluid.

In a yet further aspect, the present invention provides a device for detecting degradation in the quality of a brake fluid, comprising:
a container holding brake fluid comprising a luminescent dye, wherein there is a change in luminescence emitted by the dye in response to a change in water content of the brake fluid; and
a detector capable of detecting the change in the luminescence emitted by the dye.

The inventors have discovered that a luminescent dye can be incorporated into a brake fluid and the luminescence emitted by the dye undergoes a detectable change in response to a change in water content of the brake fluid. By detecting this change in luminescence, it is possible to detect changes in the water content of the brake fluid and it is therefore possible to detect degradation in the quality of a brake fluid.

DETAILED DESCRIPTION OF THE INVENTION

The brake fluid of the invention is preferably a glycol ether-based fluid, such as a brake fluid conforming to the DOT 3, DOT 4 or DOT 5 grades (according to the FMVSS 116). The brake fluid may comprise polyglycols.

The brake fluid comprises a luminescent dye and there is a change in luminescence emitted by the dye in response to a change in water content of the brake fluid. Preferably the luminescence increases as the water content of the brake fluid increases. Luminescent dyes may be phosphorescent dyes or fluorescent dyes, and preferably the indicator substance in the present invention is a fluorescent dye and there is a change in the fluorescence emitted by the dye in response to change in the water content of the brake fluid. WO 02/068926 discloses that fluorescent dyes may be incorporated into brake fluids so that leakage of brake fluid may be detected. However, there is no suggestion that the fluorescent dyes can be chosen such that the fluorescence varies with the water content of the brake fluid.

The fluorescent dye is preferably chosen from the group consisting of fluorescein and coumarins. The skilled person can assess whether a fluorescent dye is suitable for use in the present invention by adding the dye to a brake fluid, adding water to the brake fluid, and observing whether the emission of fluorescence varies in response to a change in water content of the brake fluid.

The amount of fluorescent dye in the brake fluid is preferably at least 1 ppm, and more preferably at least 5 ppm. Sufficient dye is required so that the change in fluorescence in response to the change in water content is detectable. The amount of fluorescent dye in the brake fluid is preferably less than 1000 ppm, and more preferably less than 200 ppm. The amount of dye is preferably minimised as it is likely to be a comparatively expensive component of the brake fluid.

The fluorescence of the dye varies in response to change in the water content of the brake fluid. Preferably, the fluorescence increases as the water content of the brake fluid increases. In a preferred embodiment of the invention, fluorescence is not detectable when the brake fluid does not comprise water, and fluorescence is detectable when the water content of the brake fluid has risen above a threshold limit. The threshold limit is a level at which the quality of the brake fluid has degraded such that the observer should be informed so that action can be taken. The threshold limit will vary with the type of brake fluid and with the braking system in which it is used, but is typically about 3-5 wt % of water based upon the weight of the brake fluid, which may correspond to a boiling temperature of about 160-170° C., depending on the grade and formulation of the particular brake fluid product.

Fluorescence occurs when photons are absorbed by the dye, causing the emission of photons with a longer wavelength. Therefore a source of excitation is needed to bring about fluorescence. Absorbance typically occurs in the ultraviolet range, so to detect the change in fluorescence it may be necessary to subject the brake fluid to ultraviolet light. It may be possible to induce the fluorescence using lasers. The device of the invention preferably comprises a source of excitation such as a laser.

The change in fluorescence may be detected using any means of detection known to the person skilled in the art. If the fluorescence is in the visible part of the infrared spectrum, the simplest means of detecting fluorescence is observation by eye. Fluorescence in the visible and other regions of the infrared spectrum can be detected by any suitable detector known in the art. Preferably the detector registers emission photons and produces a recordable output, typically as an electrical signal. The detector may detect the presence of fluorescence, may detect fluorescence above a certain threshold limit or may detect the intensity of fluorescence.

In one embodiment of the present invention, the method detects degradation in the quality of a brake fluid whilst the brake fluid is present in a braking system and the container in the device of the invention is part of the braking system, e.g. the reservoir, pipes, hoses and wheel cylinder of the braking system. In this embodiment, it is preferable to use a detector other than the human eye because it is likely to be difficult to see the brake fluid whilst it is present in the braking system. A source of excitation such as a laser is preferably present to bring about fluorescence of the brake fluid in the braking system. Preferably the detection of the change in fluorescence is achieved by detection of the brake fluid at or near a wheel cylinder. The diffusion of brake fluid within a braking system can be slow, so the quality of the brake fluid throughout a braking system may not be uniform. The quality of the brake fluid is likely to be lowest at or near the wheel cylinders where typically the brake fluid experiences most heating.

When the braking system is part of a vehicle such as a car, a motorcycle or a truck, the device of the invention is preferably incorporated into the vehicle. In a further aspect, the present invention provides a vehicle comprising a device according to the invention.

In another embodiment of the invention, the method detects degradation in the quality of a brake fluid when the brake fluid is not present in the braking system, e.g. brake fluid has been removed from a braking system or has not yet been used in a braking system. In this embodiment, the container in the device of the invention may be any container suitable for holding braking fluid, e.g. a bottle.

The method of the invention preferably further comprises a step of informing an observer of the change in luminescence emitted by the dye in response to a change in water content of the brake fluid. The device of the invention preferably further comprises a display that informs an observer of the change in the luminescence. The observer is thereby informed of a change in the water content of the brake fluid and a degradation in the quality of the brake fluid, and can take appropriate action such as changing the brake fluid in a braking system, or ceasing to use a vehicle. Preferably the observer is directly informed of the appropriate action, e.g. the display informs the observer to change the brake fluid, or to cease driving the vehicle.

EXAMPLES

The invention will now be described by reference to examples which are not intended to be limiting of the invention.

Fluorescent dyes were dissolved in a glycol ether-based brake fluid from Shell Chemicals, conforming to the DOT 4 standard. Table 1 indicates the type and amount of dye that were used and indicates the amount of water that was added to the mixtures of dye and brake fluid. The fluids were placed in an irradiation cabinet consisting of two ultraviolet lamps with a dual wavelength of 254 nm and 366 nm. Visual observation was used to detect the fluorescence of the fluid. Table 1 shows that three fluorescent dyes (examples 1-3) were identified where there is a change in the fluorescence emitted by the dye in response to a change in the water content of the brake fluid. For two other dyes (comparative examples 1-2), no change in fluorescence was observed.

TABLE 1

| | Dye | Ratio of brake fluid:water | Dye concentration of total mixture | Fluorescence |
|---|---|---|---|---|
| Example 1 | Fluorescein sodium | No water | 100 ppm | No |
| | | 3:1 | 75 ppm | Yes |
| | | 1:1 | 50 ppm | Yes |
| | | 1:3 | 25 ppm | Yes |
| Comparative Example 1 | Rhodamine B | No water | 100 ppm | Yes |
| | | 1:1 | 50 ppm | Yes |
| Comparative Example 2 | Rhodamine 6G | No water | 100 ppm | Yes |
| | | 1:1 | 50 ppm | Yes |
| Example 2 | Coumarin 4 | No water | 100 ppm | No |
| | | 1:1 | 50 ppm | Yes |
| Example 3 | 4-Hydroxycoumarin | No water | 100 ppm | No |
| | | 1:1 | 50 ppm | Slightly |

What is claimed is:

1. A method for detecting degradation in the quality of a brake fluid, wherein the brake fluid comprises a luminescent dye in an amount such that there is a detectable change in luminescence emitted by the dye in response to an increase in water content of the brake fluid to above about 3 wt % based upon the weight of the brake fluid, comprising a step of detecting changes in the luminescence emitted by the dye.

2. A method according to claim 1, wherein the luminescent dye is a fluorescent dye.

3. A method according to claim 1, wherein the brake fluid is in a braking system.

4. A method according to claim 1, further comprising a step of informing an observer of the change in the luminescent dye.

5. A device for detecting degradation in the quality of a brake fluid, comprising:
- a container holding brake fluid comprising a luminescent dye in an amount such that there is a detectable change in luminescence emitted by the dye in response to an increase in water content of the brake fluid to above about 3 wt % based upon the weight of the brake fluid; and
- a detector capable of detecting the change in the luminescence emitted by the dye.

6. A device according to claim 5, comprising a display that informs an observer of the change in the luminescent dye.

7. A device according to claim 5, further comprising a source of excitation capable of bringing about luminescence of the luminescent dye.

8. A device according to claim 5 wherein the detectable change is in response to an increase in water content to above about 5 wt %.

* * * * *